(12) United States Patent
Spinoza

(10) Patent No.: US 8,361,034 B2
(45) Date of Patent: Jan. 29, 2013

(54) METHOD AND APPARATUS FOR SECURING A LINE TO A PATIENT

(75) Inventor: Marc Howard Spinoza, London (GB)

(73) Assignee: Braidlock Limited, London (GB)

( * ) Notice: Subject to any disclaimer, the term of this patent is extended or adjusted under 35 U.S.C. 154(b) by 979 days.

(21) Appl. No.: 11/995,492

(22) PCT Filed: Jul. 5, 2006

(86) PCT No.: PCT/GB2006/002481
§ 371 (c)(1),
(2), (4) Date: Jul. 25, 2008

(87) PCT Pub. No.: WO2007/007043
PCT Pub. Date: Jan. 18, 2007

(65) Prior Publication Data
US 2009/0221970 A1    Sep. 3, 2009

(30) Foreign Application Priority Data
Jul. 13, 2005 (GB) .................... 0514424.1

(51) Int. Cl.
*A61M 5/32* (2006.01)
(52) U.S. Cl. ....................................... 604/174
(58) Field of Classification Search ................ 604/174, 604/177–180; 128/207.17
See application file for complete search history.

(56) References Cited

U.S. PATENT DOCUMENTS

| | | | |
|---|---|---|---|
| 656,187 A | 9/1900 | Gunnel | 285/148.13 |
| 2,017,625 A | 10/1935 | Kellems | 294/86.42 |
| 2,766,501 A | 11/1956 | Loyal | 294/86.42 |
| 3,122,806 A | 3/1964 | Lewis | 403/220 |
| 3,368,564 A | 2/1968 | Selix | 604/180 |
| 3,487,837 A | 1/1970 | Petersen | 128/349 |
| 3,883,102 A | 5/1975 | Trigg | 248/75 |
| 3,907,003 A | 9/1975 | Regner et al. | 138/118.1 |
| 4,411,654 A | 10/1983 | Boarini et al. | 604/165.04 |
| 4,509,877 A | 4/1985 | Sobin et al. | 403/41 |
| 4,533,349 A | 8/1985 | Bark | 604/174 |
| 4,754,685 A | 7/1988 | Kite et al. | 87/9 |
| 4,867,154 A | 9/1989 | Potter et al. | 128/207.17 |
| 4,906,234 A | 3/1990 | Voychehovski | 604/79 |
| 5,129,891 A | 7/1992 | Young | 604/533 |
| 5,147,322 A | 9/1992 | Bowen et al. | 604/180 |

(Continued)

FOREIGN PATENT DOCUMENTS

| | | |
|---|---|---|
| DE | 19522301 | 1/1997 |
| EP | 0009893 | 4/1980 |

(Continued)

OTHER PUBLICATIONS

"Communication pursuant to Article 96(2) EPC," Official action of the European Patent Office in European Application No. 04021343, dated Apr. 11, 2007.

(Continued)

*Primary Examiner* — Christopher D Koharski
(74) *Attorney, Agent, or Firm* — Fulbright & Jaworski L.L.P.

(57) ABSTRACT

Apparatus for securing a line (112), comprising at least one sleeve (110) of variable length capable when lengthened of gripping the line and when shortened of sliding along the line, the device further comprising release means (214, 216) arranged to shorten the sleeve on application of a compressive force to the release means in a direction substantially transverse to the longitudinal direction of the sleeve.

18 Claims, 19 Drawing Sheets

U.S. PATENT DOCUMENTS

| | | | |
|---|---|---|---|
| 5,152,298 A | 10/1992 | Kreyenhagen et al. | 607/116 |
| 5,188,101 A | 2/1993 | Tumolo | 128/207.18 |
| 5,201,357 A | 4/1993 | Kuhn et al. | 164/132 |
| 5,221,265 A | 6/1993 | List | 604/180 |
| 5,232,453 A | 8/1993 | Plass et al. | 604/180 |
| 5,257,975 A | 11/1993 | Foshee | 604/105 |
| 5,292,312 A | 3/1994 | Delk et al. | 604/180 |
| 5,344,406 A | 9/1994 | Spooner | 604/179 |
| 5,370,627 A | 12/1994 | Conway | 604/180 |
| 5,395,344 A | 3/1995 | Beisang et al. | 604/180 |
| 5,437,650 A | 8/1995 | Larkin et al. | 604/536 |
| 5,460,170 A * | 10/1995 | Hammerslag | 600/201 |
| 5,476,493 A | 12/1995 | Muff | 607/119 |
| 5,480,203 A | 1/1996 | Favalora et al. | 294/86.42 |
| 5,505,117 A | 4/1996 | Dunlap et al. | 87/1 |
| 5,507,733 A | 4/1996 | Larkin et al. | 604/534 |
| 5,662,616 A | 9/1997 | Bousuet | 604/175 |
| 5,743,885 A | 4/1998 | Hoerby | 604/180 |
| 5,836,913 A | 11/1998 | Orth et al. | 604/107 |

FOREIGN PATENT DOCUMENTS

| | | |
|---|---|---|
| EP | 0137880 | 4/1985 |
| EP | 0516876 | 12/1992 |
| EP | 1512640 | 3/2005 |
| GB | 2061372 | 5/1981 |
| GB | 1601334 | 10/1981 |
| JP | 55-16650 | 2/1980 |
| JP | 06-327776 | 11/1994 |
| JP | 10-248941 | 9/1998 |
| RU | 1836114 A3 | 8/1993 |
| WO | WO 81/01519 | 6/1981 |
| WO | WO 82/03775 | 11/1982 |
| WO | WO 91/14034 | 9/1991 |
| WO | WO 92/06235 | 4/1992 |
| WO | WO 93/25264 | 12/1993 |
| WO | WO 95/29727 | 11/1995 |
| WO | WO 97/21459 | 6/1997 |
| WO | WO 99/10250 | 3/1999 |
| WO | WO 03/090835 | 6/2003 |
| WO | WO 03/105727 | 12/2003 |

OTHER PUBLICATIONS

Derwent Accession No. 95-129939/9517, "New born baby naval vein catheterisation device—has sleeve with cap on its non-working end and internal catheter duct," Abstract of Patent No. SU1836114, published Aug. 23, 1993.

Office Communication, issued in U.S. Appl. No. 09/506,361, dated May 22, 2002.

Office Communication, issued in U.S. Appl. No. 09/506,361, dated Aug. 1, 2002.

Office Communication, issued in U.S. Appl. No. 09/506,361, dated Apr. 8, 2003.

Office Communication, issued in U.S. Appl. No. 09/506,361, dated Jan. 9, 2004.

Office Communication, issued in U.S. Appl. No. 09/506,361, dated Mar. 12, 2004.

Office Communication, issued in U.S. Appl. No. 09/506,361, dated Jul. 13, 2005.

Office Communication, issued in U.S. Appl. No. 09/506,361, dated Dec. 1, 2005.

Office Communication, issued in U.S. Appl. No. 09/506,361, dated Jun. 5, 2006.

Office Communication, issued in U.S. Appl. No. 09/506,361, dated Nov. 29, 2007.

Office Communication, issued in U.S. Appl. No. 09/506,361, dated Jun. 24, 2008.

Office Communication, issued in United Kingdom Patent Application No. GB0514424.1, dated Mar. 10, 2010.

Office Communication, issued in U.S. Appl. No. 11/995,492, dated Jun. 11, 2009.

Office Communication, issued in U.S. Appl. No. 09/506,361, dated Jun. 11, 2009.

Office Communication, issued in U.S. Appl. No. 09/506,361, dated Dec. 29, 2008.

* cited by examiner

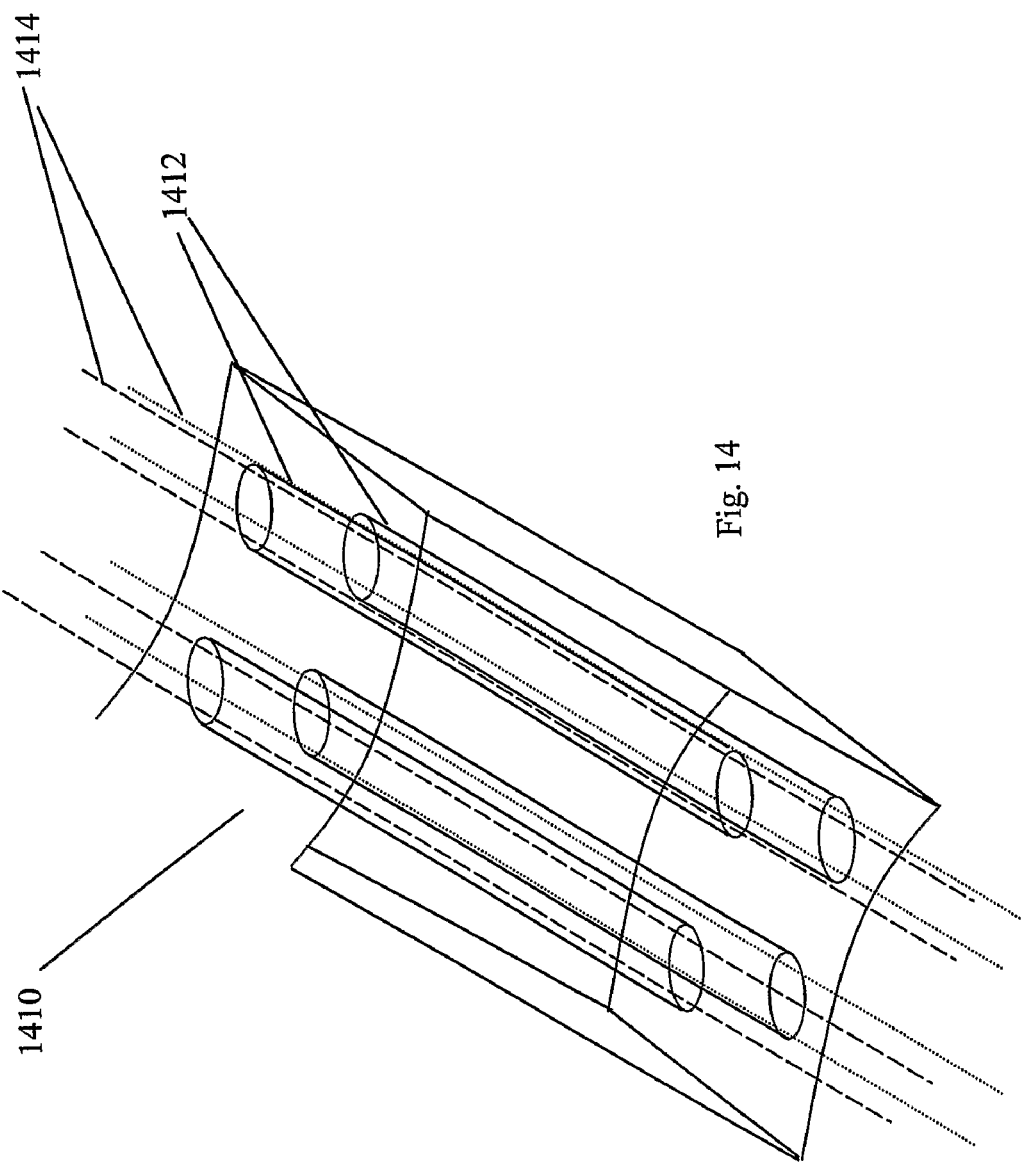

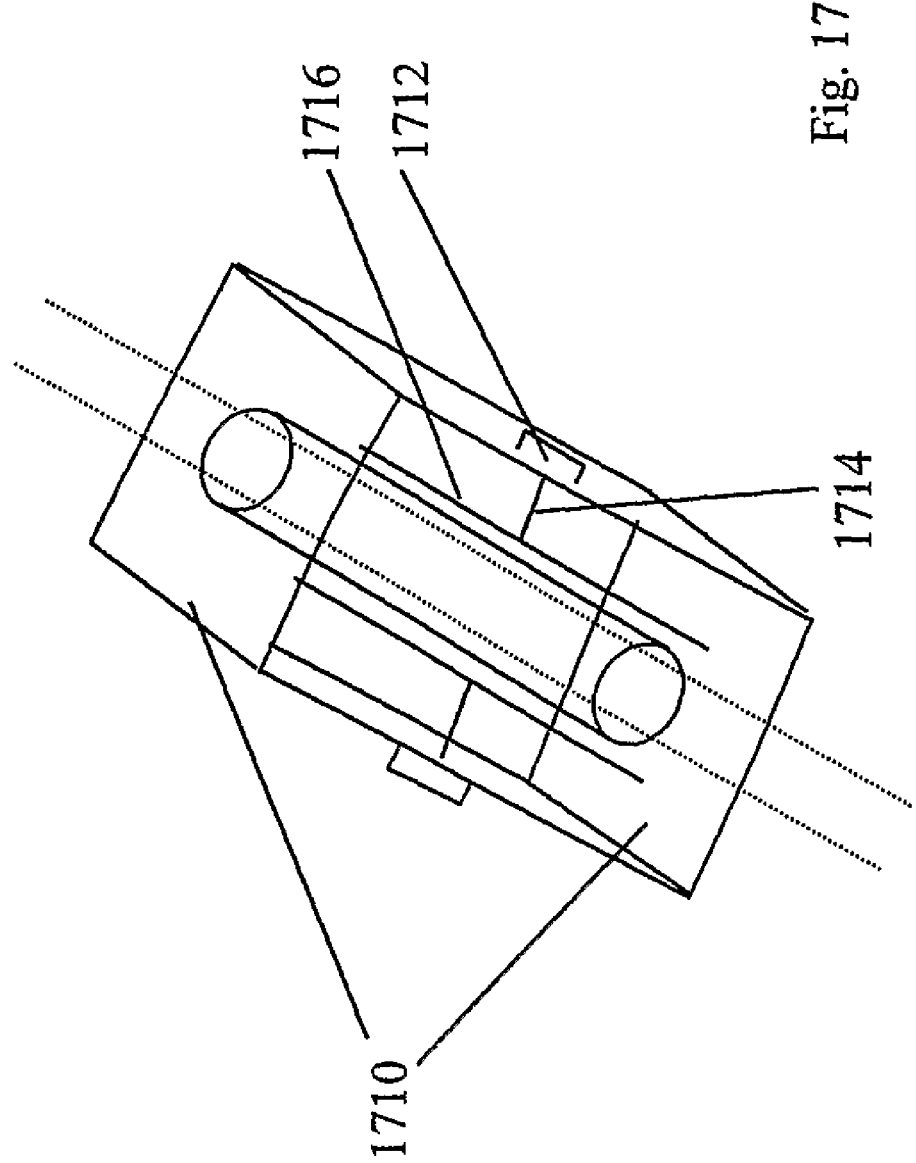

METHOD AND APPARATUS FOR SECURING A LINE TO A PATIENT

This application is a national phase application under 35 U.S.C. §371 of International Application No. PCT/GB2006/002481 filed 5 Jul. 2006, which claims priority to UK Patent Application No. 0514424.1 filed 13 Jul. 2005, the contents of which are incorporated herein by reference in their entirety.

The present invention relates to the field of fasteners and, in particular, to medical or surgical fasteners for securing the positions of medical lines.

EP-B-1007430 and EP-A-1512640 describe apparatus for simply and effectively locking the position of a line, such as a tube or wire, and in particular fixing a line in relation to a patient into whom the line is inserted. The device, which is described in more detail below in relation to FIGS. 1 and 11 to 13, comprises a sleeve through which the line passes. Compression of the sleeve length-wise widens the sleeve radially, allowing the line to slide through the sleeve freely. On release, the sleeve lengthens and constricts radially, gripping the line and preventing movement of the line relative to the sleeve. Any further tension applied to the line or the sleeve itself tightens the grip of the sleeve around the line, further restricting movement of the line.

The sleeve may be provided with attachment means to attach the sleeve, and so secure the line, directly to a patient and/or to equipment, such as a bed or monitoring device, associated with the patient. The attachment means may comprise, for example, suture loops to allow the line to be sutured to a patient or a bandage or other wound-covering or the attachment means may comprise an adhesive means, such as an adhesive pad. In a further embodiment, the attachment means may comprise means for attaching the sleeve to a strap or mask, which may then be attached around a patient or an item of equipment.

As will be appreciated by one skilled in the art, such apparatus has a large number of uses for securing different types of lines. One such use may be in attaching a breathing tube to a neonatal baby.

It has been appreciated that, in some embodiments, it can be difficult to access the ends of the sleeve to compress the sleeve and allow movement of the line. In particular, two hands may be required to compress the sleeve, or to compress one end of the sleeve whilst holding the other still. In some situations, whilst it may not be necessary to access both ends of the sleeve directly, the sleeve may be located in a confined space. For example it may be difficult to access apparatus attached to a breathing line for a neonatal baby at a mouthpiece, since the components may be quite small and lie close to the baby's face.

According to one aspect, there is therefore provided apparatus for securing a line, comprising a sleeve of variable length capable when lengthened of gripping the line and when shortened of sliding along the line, the device further comprising release means arranged to shorten the sleeve on application of a compressive force to the release means in a direction substantially transverse to the longitudinal direction of the sleeve.

Advantageously, providing release means to compress the sleeve allows easier release of the line from the sleeve. In particular, it has been found that applying a transverse 'pinching' movement to a release means is easier to perform, particularly single-handedly, than applying direct longitudinal pressure to cause shortening of the sleeve. Further, providing release means may enable release of the sleeve without the operator requiring access to both ends of the sleeve. This may be particularly advantageous if the sleeve is located in an inaccessible place, for example attached to a breathing tube for a baby, when it may be difficult or disturbing for the patient to access the end of the sleeve close to the face.

In a preferred embodiment, the release means further comprises biasing means arranged to bias the line to a lengthened position. The biasing means may provide an additional force lengthening the sleeve and so providing additional grip for the sleeve on the line. The biasing means may be formed integrally with the release means, for example, the release means may be attached to the sleeve in such a way as to impart a biasing force to the sleeve. In an alternative embodiment, the biasing means may comprise, for example, a spring attached to both ends of the sleeve and arranged so that the sleeve lies along the axis of the spring.

In one embodiment, the apparatus may further comprise means to secure the apparatus directly to a patient.

In an alternative embodiment, the apparatus further comprises means to secure the apparatus to furniture or equipment associated with a patient, for example to the patient's bed or to monitoring equipment attached to or associated with the patient. In this way, the apparatus may be secured relative to the patient without having to secure the apparatus directly to the patient themselves.

Preferably, the release means is operable from one end of the sleeve. This may enable a line to be released by an operator accessing only one end of the sleeve.

In a further embodiment, the release means may be operable from either end of the sleeve. Hence the release means may be operated from either end as is convenient.

In a preferred embodiment, the release means is attached to attachment points at the ends of the sleeve and the application of a compressive force to the release means brings the attachment points closer together, hence shortening the sleeve.

Preferably, the compressive force applied to the release means to shorten the sleeve is less than the longitudinal force required to shorten the sleeve. Hence the sleeve can be released more easily when a force is actively applied, but the use of release means to shorten the sleeve may mean that slippage of the sleeve along the line and other accidental movements are less likely.

Preferably, the compressive force is applied to the release means by manually pinching a portion of the release means. Advantageously, this may allow the sleeve to be compressed using one hand, since a pinching force may be applied with one hand.

Preferably, the pinching force required to shorten the sleeve is less than around 200N, further preferably less than around 150N.

Preferably, the pinching force required to shorten the sleeve is at least around 20N, further preferably at least around 30N.

Preferably, the longitudinal force required to shorten to sleeve is at least around 50N.

In one embodiment, the release means may comprise a flexible member attached to the sleeve.

Preferably, the member is arranged so that a compressive force applied to the member in a direction substantially transverse to the longitudinal direction of the sleeve, bends the member and shortens the sleeve. The compressive force may be applied to the member by pinching the member between the operator's fingers. This may bend the member to a concave position, in towards the sleeve, shortening the sleeve to release the line.

Preferably, the compressive force may be applied along the outer edges of the member.

In one embodiment, the outer edges of the member are maintained in a fixed position relative to the opposing end of the sleeve by support means. For example, the support means may comprise rigid or fixed-length supports coupled to the other end of the sleeve. Hence any movement of the centre of the member relative to the edges of the member may cause a lengthening or shortening of the sleeve.

In a preferred embodiment, the member is held in a concave position when the sleeve is at its maximum length to bias the sleeve to a lengthened position. This may provide an additional biasing force to increase the grip of the sleeve on the line. In addition, maintaining the member in a flexed or bent position may make it easier to operate the release means and may ensure that the compressive force acts on the sleeve in the direction to shorten the sleeve.

In some embodiments, one end of the sleeve may be fixed in position relative to a patient or item of equipment. In particular, one end of the sleeve may be coupled to a mouthpiece for breathing apparatus.

In one embodiment, the release means may be arranged to provide an initial resistance to movement on application of the compressive force.

In a preferred embodiment, the sleeve comprises a braided tubular sleeve. This may enable a line to be gripped securely but evenly over its circumference. Gripping the line in this way may enable the line to be gripped without crushing any lumen passing through the line.

In one embodiment, the apparatus comprises a plurality of sleeves for securing a plurality of lines. Hence a single release means may be used to operate a plurality of sleeves. This may be particularly useful when a plurality of lines are directed to a similar area on a patient and may mean that a plurality of lines can be secured by securing only one piece of apparatus relative to the patient.

In one embodiment, the apparatus further comprises a marker opaque to radiation. Preferably, the marker comprises at least one filamentary strand of opaque material woven into the sleeve.

Apparatus according to any preceding claim wherein the force required to shorten the sleeve is greater than the force required to cause the flexible line to buckle.

As described in EP-B-1007430 and EP-A-1512640, a standard method of securing a line, such as a tube or a wire, to a patient is to use adhesive tape attached between the patient's body and the line. In order to ensure that the line is safely secured to the patient, it can be necessary to provide a large covering of adhesive tape over a large area around the point at which the line is inserted.

Since the method of securing the line to the patient involves covering a large area around the insertion point with adhesive tape, it can be difficult to ensure that the line has been inserted into the patient to the correct depth and to ensure that the line has not just gathered and looped itself around outside the patient's body under the adhesive tape. Further, even if a line is inserted correctly in the first place, the line may work its way out of the body underneath the tape, which may be difficult to detect externally.

This is a particular problem in situations where it is important to ensure that the line is inserted into the patient to a predetermined depth. To enable accurate positioning of the line, gradations may be provided on the line. Once the line has been positioned accurately, it may then be secured into place, but as set out above, the gradation visible on the outside of the adhesive may not accurately reflect the length of the line that is inserted into the patient.

As described in EP-B-1007430 and EP-A-1512640, a line locking device may be provided to reduce the amount of adhesive tape around the insertion site, hence increasing visibility and enabling a user to ensure that the line remains correctly inserted. However, in some situations, for example if dressings are provided around the insertion site, it still may not be possible to observe visibly the line entering the patient.

Hence, according to one aspect, there is provided apparatus for securing a line to a patient, comprising a sleeve of variable length capable when lengthened of gripping the line and when shortened of sliding along the line, the apparatus further comprising a marker opaque to radiation, wherein the marker comprises at least one filamentary strand of opaque material woven into the sleeve.

An opaque marker may enable the position of the line locking device, and hence the position of the line relative to the patient, to be determined on an image of the patient. This may allow an operator to determine whether there are loops of the line lying between the locking device and the patient and hence whether the line is incorrectly positioned with respect to the patient, for example by having worked itself out of the patient's body.

Advantageously, the marker is opaque to X-ray radiation so that the position of the device on an X-ray image may be determined.

It has further been appreciated that, for some patients, a number of different lines may be inserted into the body in a localised area. Providing line locking devices which include markers visible by X-ray enables the positions of the lines to be identified, but it can be difficult to determine which marker corresponds to which line entering the body.

According to a further aspect, there is provided apparatus for securing a plurality of lines to a patient, comprising a plurality of sleeves of variable length capable when lengthened of gripping the line and when shortened of sliding along the line, each sleeve having an associated marker, wherein the markers comprise filamentary strands of material opaque to radiation woven into the sleeves and wherein the markers corresponding to the sleeves are mutually distinct.

Preferably the markers are mutually distinct when viewed on an X-ray image. This may enable different lines to be individually identified on the image.

In a preferred embodiment, each sleeve may have an associated marker comprising a different number of filamentary strands of material.

Since the apparatus described herein may be deployed to fix the position of a line over an extended period of time, it has been appreciated that it is important for the apparatus to resist even small movements along the line, for example caused by movement of the patient, which may build up over time to a be significant movement of the line relative to the patient. In particular, the locking device should resist movement of the line when the line is pushed towards the patient.

There is therefore provided herein apparatus for securing a flexible line with respect to a patient, comprising a sleeve of variable length capable when lengthened of gripping the line and when shortened of sliding along the line, wherein the force required to shorten the sleeve is greater than the force required to cause the flexible line to buckle.

Preferably, the sleeve comprises a woven sleeve and the force required to shorten the sleeve may be determined based on the stiffness of the braid of the sleeve.

That is, to prevent small movements of the line relative to the apparatus, the force required to shorten the sleeve, for example to overcome the stiffness of the woven braid, should exceed the flexibility of the line. With the apparatus arranged in this way, any longitudinal pressure applied on the line to push it towards the sleeve will cause the line to bend before causing the sleeve to shorten and pushing the line through the sleeve. This is described and illustrated in more detail below with reference to FIGS. 10a and 10b.

The line may comprise a tube having an external diameter of around 5 mm and an internal diameter of around 4 mm.

Preferably, the force required to shorten the sleeve is at least around 50N, further preferably at least around 100N.

Medical lines are often designed to carry fluids to or from a patient, for example catheter tubes or drip lines may be inserted into patients. It is quite common for these lines to develop holes or splits whilst in use, particularly if the lines are in use over an extended period of time. Whilst some lines may be repaired in the short term using adhesive tape, this will not fix the line over the longer term, hence a damaged or split line may require the line to be replaced in the patient with a new line. This may cause additional trauma to the patient.

According to a further aspect, there is described herein a method of sealing an aperture in a line for a patient, comprising applying a sleeve over the aperture, the sleeve being of variable length and capable when lengthened of gripping the line and when shortened of sliding along the line, wherein the sleeve is lengthened to grip the line when applied over the aperture, hence sealing the aperture.

Due to the radially constricting pressure applied by the sleeve of the line locking device to the line, an additional or alternative use of the locking device may be to repair leaks in lines. In particular, the locking devices may be used to repair a split line by compressing the split edges of the line together and resealing the line. The line locking device may further be provided with a fluid-resistant coating on the internal surface of the sleeve to provide a water-tight seal around a hole or split in a line.

Aspects of the method and apparatus described above may be provided independently or in combination and preferred features of one aspect may be applied to other aspects.

Embodiments of the methods and apparatus described herein will now be described with reference to the figures in which:

FIG. 14 illustrates a further embodiment of a line locking device including a plurality of sleeves for securing a plurality of lines;

FIG. 17 illustrates a line locking device according to a further embodiment.

A prior art line locking device, as described in EP-B-1007430 and EP-B-1512640 will now be described in more detail with reference to FIGS. 1 and 11 to 13.

Figure 1:
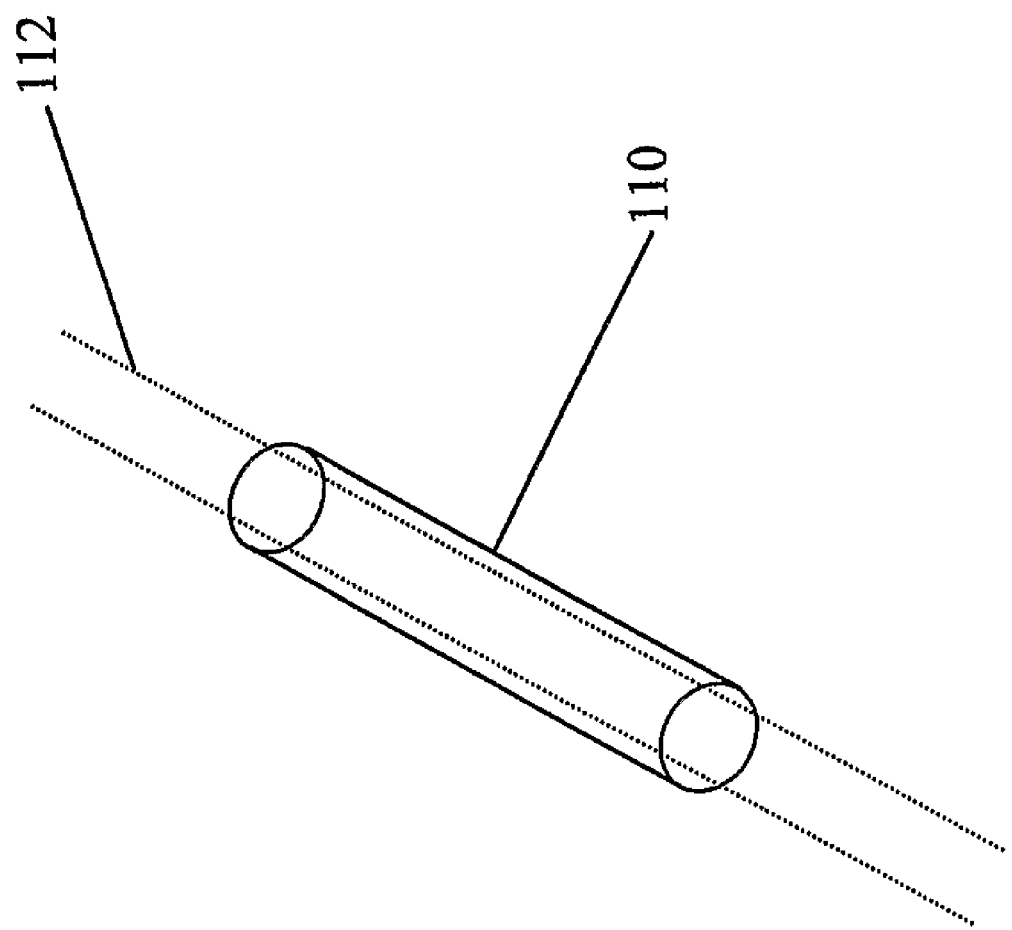
FIG. 1 is a schematic diagram of a prior art line locking device according to one embodiment.

FIG. 1 illustrates a line locking device in the form of a sleeve 110. The width of the sleeve 110 is expandable by compressing the sleeve in the longitudinal direction. Expansion of the sleeve width permits the insertion of a line 112, for example a tube, into the sleeve (or permits the sleeve 110 to slide over the line 112). Once the line 112 has been inserted, the sleeve 110 may be released and the sleeve 110 springs back to its extended position, which causes the width of the sleeve to decrease allowing the sleeve 110 to grip the line 112.

Figure 11:
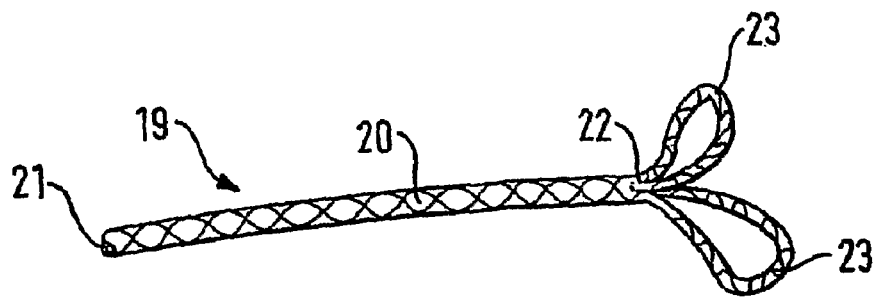
FIG. 11 illustrates a prior art line locking device according to one embodiment.

Referring then to FIG. 11, the fastener 19 or line locking device includes a generally tubular sleeve 20 defined by helically-wound and interwoven or intertwined filaments of nylon. The wall of the sleeve 20 may therefore be described as a braid or plait of foraminous or perforated mesh, grid, net or web, defining numerous openings which can be expanded or contracted as will become evident.

One end of the sleeve 21 is open and the other end 22 is closed. The closed end 22 includes attachment means in the form of loops 23 formed by doubling back and laterally compressing an end of the sleeve 20 and inserting the compressed end back into the sleeve 20 through an opening in its wall. The doubled-back sleeve 20 is glued in place so as to hold the loop formation.

For use in anchoring umbilical lines, the sleeve 20 preferably measures approximately 1 mm in internal diameter and 200 mm in overall length when at rest, with the loops 23 being around 20 mm in diameter.

Figure 12A:
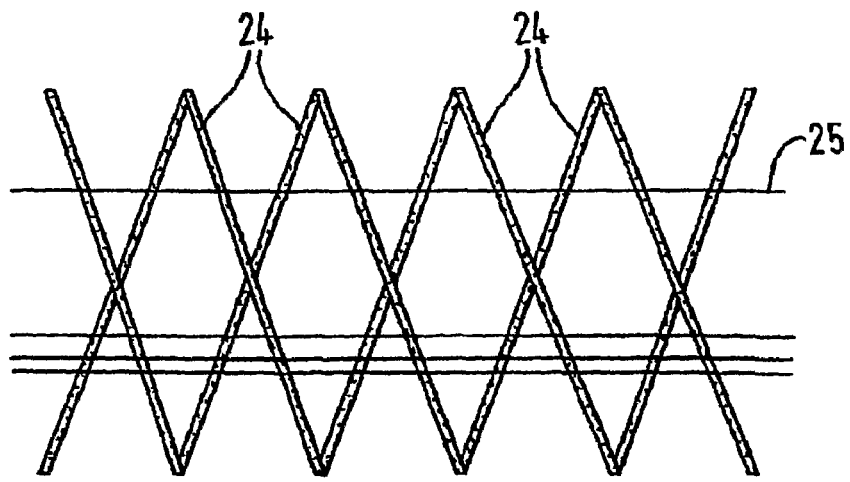
FIGS. 12a and 12b illustrate a shortened and lengthened sleeve of a locking device according to one embodiment.
Figure 12B:
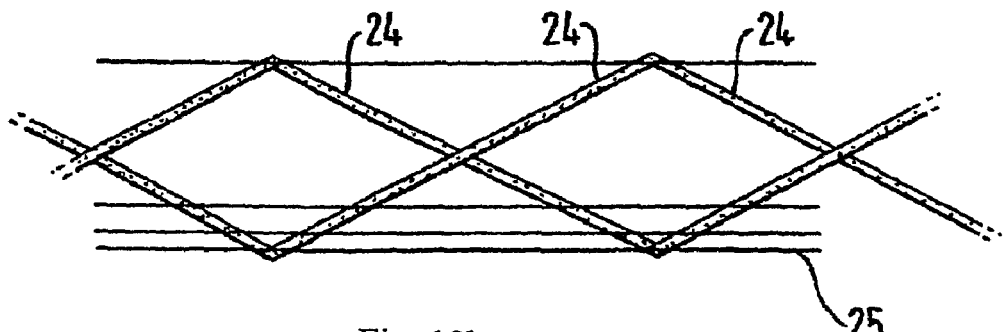

A notable characteristic of the sleeve 20 is that its length can readily be varied by axial compression or tension and that this variation in length has a direct and marked effect upon the diameter of the sleeve 20. Elongation causes the sleeve 20 to narrow whereas shortening the sleeve 20 makes it wider. The helically-wound construction promotes this effect as shown in FIGS. 12(a) and 12(b). In these diagrams, the filaments 24 are shown schematically as intersecting hoops, shown edge-on, that lie at mutually opposite and equal angles with respect to the longitudinal axis of the sleeve 20.

In FIG. 12(a), the sleeve 20 is shown in a compressed condition with the filaments 24 bunched up. The filaments 24 lie at a relatively large angle to the longitudinal axis of the sleeve 20, and the transverse diameter of the sleeve 20 is therefore at a maximum. FIG. 12(b), in contrast, shows the sleeve 20 in an elongated condition. In this instance, the filaments 24 lie at a relatively small, more acute angle with respect to the longitudinal axis of the sleeve 20 and hence the transverse diameter of the sleeve 20 is at a minimum. In this elongated and narrow state, the filaments tightly grip a line 25.

With reference now to the series of illustrations in FIGS. 13(a) to 13(l), the sequence of steps involved in using a sleeve 20 to locate an umbilical line 25 will be described.

Figure 13A:
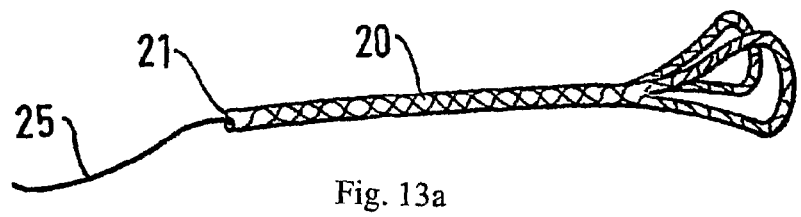
FIGS. 13a to 13l illustrate schematically the process of securing a line to a patient using a line locking device.
Figure 13B:
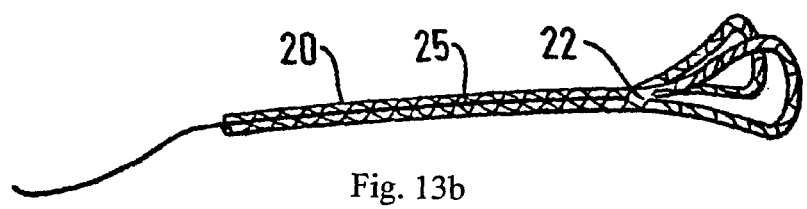
Figure 13C:
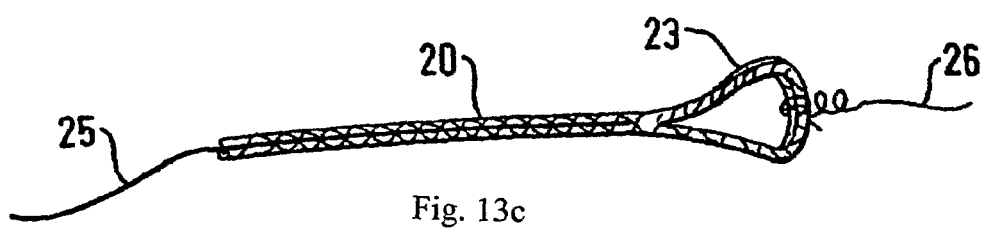
Figure 13D:
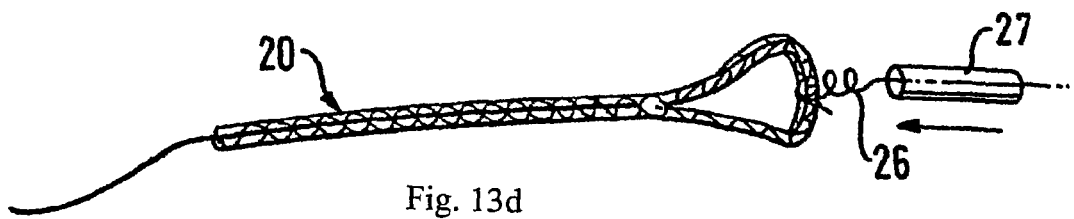
Figure 13E:
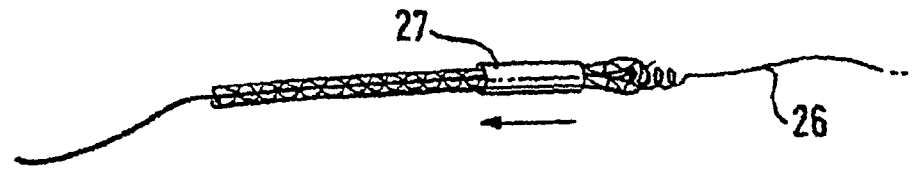
Figure 13F:
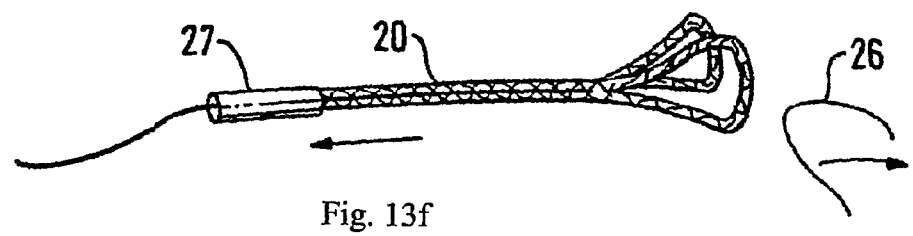
Figure 13G:
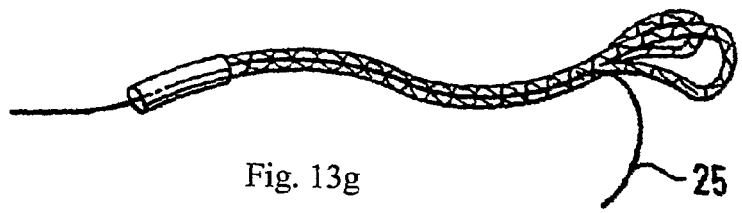
Figure 13H:
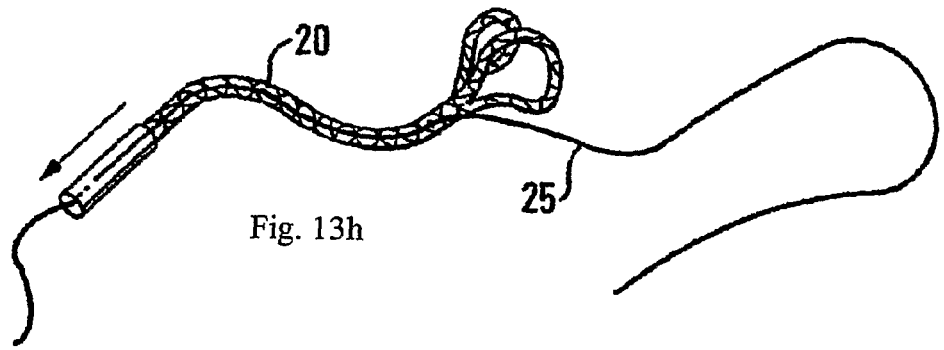
Figure 13I:
Figure 13J:
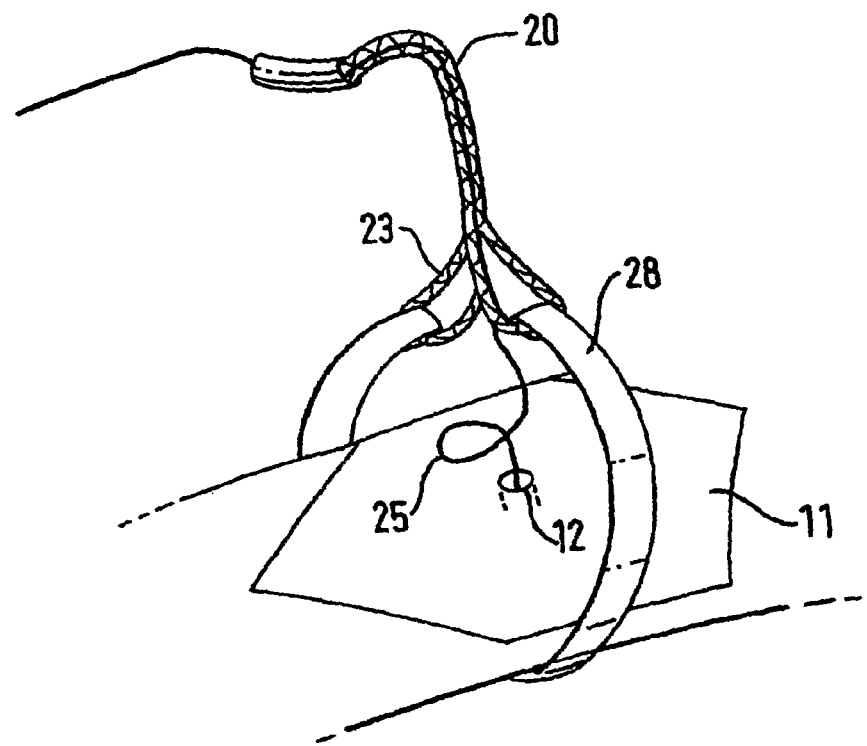
Figure 13K:
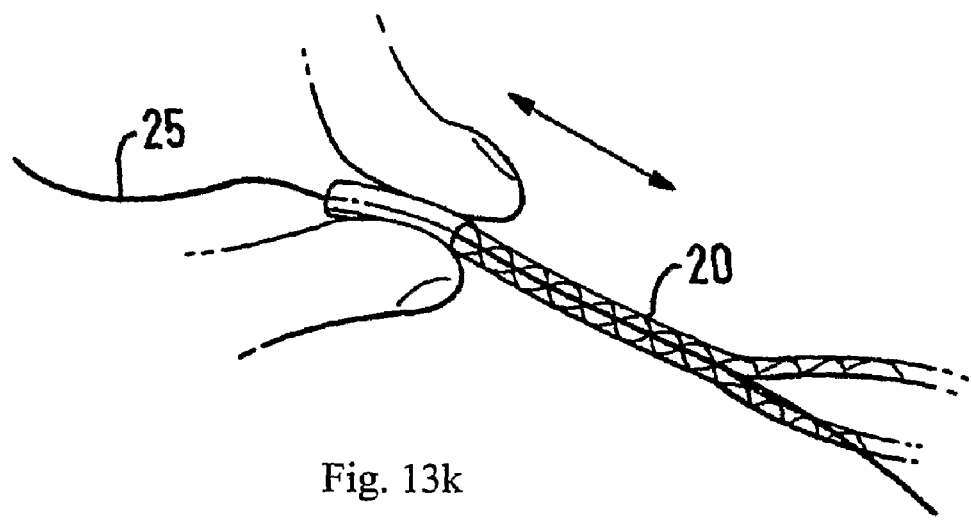
Figure 13L:
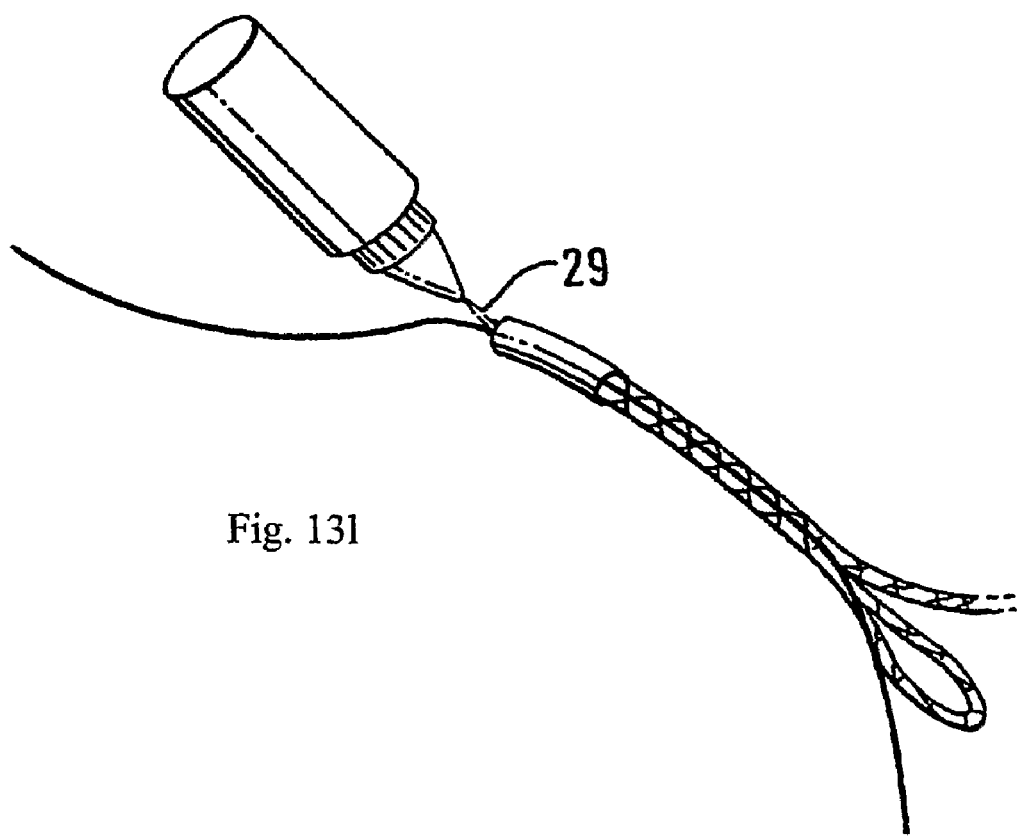

First of all and referring in this regard to FIG. 13(a), an umbilical line 25 is threaded into the open end 21 of the sleeve 20. In FIG. 13(b), the line 25 is shown being fed up the sleeve 20 towards the closed end 22. The progress of the line 25 within the sleeve 20 is eased by gripping the sleeve 20 with the fingers and longitudinally compressing it to shorten it and hence widen its internal diameter. This allows the line 25 to slide freely within the sleeve 20.

Once the line 25 nears the closed end 22 of the sleeve 20, a monofilament 26 is tied to the pair of loops 23 as shown in FIG. 13(*c*). Then a silicone rubber collar 27 of about 20 mm in length and 2 mm in diameter is threaded onto the monofilament 26 (FIG. 13(*d*)) and slid along it and over the sleeve 20 (FIG. 13(*e*)) until it covers the open end 21 of the sleeve 20, at which point the monofilament 26 is untied and discarded (FIG. 13(*f*)). The collar 27 holds together the free ends of the filaments 24 making up the sleeve 20 and so prevents the open end 21 of the sleeve 20 from fraying and unravelling.

The line 25 is then passed through one of the openings in the sleeve wall (FIG. 13(*g*)) near its closed end 22, following which the sleeve 20 is again longitudinally compressed and slid up along the line 25 pulling through as much line 25 as is required (FIG. 13(*h*)).

At this stage, the line 25 is ready to be introduced into the umbilicus 12 of a premature infant 11 as shown in FIGS. 13(*i*) and 13(*j*). Once the line 25 has been inserted into the umbilicus 12 and its position correctly located, the line 25 is sutured to the umbilicus 12. A harness 28 is passed around the baby's abdomen and attached to the loops 23 of the sleeve 20 as shown in FIG. 13(*j*). It is also possible to attach the sleeve 20 directly to the umbilical stump, preferably by suturing.

Final adjustments to the line 25 are made and then the sleeve 20 is ready to be locked to the line 25. This is achieved by tensioning the sleeve 20 by pulling it over the line 25 as shown in FIG. 13(*k*) to elongate and narrow it. In doing so, the helically woven filaments frictionally engage the line 25, collectively imparting an evenly distributed and firm but gentle compressive gripping force over a large area of the line 25. This ensures that the line 25 is secured without restricting its lumen, as could happen if a point or edge loading were applied to the line 25.

The gripping force exerted by the sleeve 20 naturally increases the frictional forces that resist axial movement of the line 25 with respect to the sleeve 20. Moreover, once the compressive and hence frictional forces rise above a certain threshold, it will be clear that further attempts to move the line 25 axially with respect to the sleeve 20 will meet with increased compression and frictional forces that tend to resist the movement ever more strongly without allowing further slippage. This gives rise to a locking effect.

Release of the line 25 is possible simply by longitudinally compressing the sleeve 20 to expand it away from the line 25, thereby allowing adjustments to be made by sliding the line 25 within the sleeve 20. The line 25 can be locked again when desired.

It has been found during testing that the line 25 will break—under loads far in excess of anything encountered in normal use—rather than slip within the sleeve 20 once locked in this way. Nevertheless, in a final optional step, permanent fixing of the sleeve 20 in relation to the line 25 can be achieved by applying medical super glue 29 such as Braun Hystoacryl (trade mark) between the sleeve 20 and the line 25 as shown in FIG. 13(*l*).

An embodiment of a line locking device that includes a release and additional biasing means will now be described with reference to FIG. 2.

In the illustrated embodiment, the sleeve 110 is further provided with release members 214, 216 which are joined along their outer edges by side supports 218, 220. The release members 214, 216 are joined to the sleeve 110 of the line locking device at each end of the sleeve, maintaining the apertures at each end of the sleeve 110 to allow the line 112 to be inserted. The release members 214, 216 are joined to the side supports 218, 220 along their outer edges. In the present embodiment, the side supports 218, 220 are slightly longer than the sleeve 110 of the line locking device, so that the release members 214, 216 are held in a curved configuration at each end of the sleeve. As illustrated in FIG. 2, the release members 214, 216 are held as two concave surfaces facing away from each end of the sleeve 110.

The release members 214, 216 are preferably manufactured from a resilient material, which is biased to return towards a planar configuration. Since the side supports 218, 220 of the device have a fixed length, the release members 214, 216 of the present embodiment also exert a longitudinal tension on the sleeve 110, causing the sleeve 110 to be biased to a lengthened position and hence constricting the width of the sleeve 110, which allows the sleeve to grip the line 112 more securely.

Advantageously, to release a line 112 inserted into the sleeve 110, the width of the sleeve can be increased simply by squeezing together the outer edges of one or both of the release members 214, 216 in the directions shown in the arrows 222, 224, causing one or both of the release members 214, 216 to bend further towards the middle of the device. Since the outer edges of the release members are held at a fixed distance by the side supports 218, 220, this causes longitudinal compression of the sleeve 110 and an increase in the width of the sleeve 110, allowing the line to move freely within the sleeve. It will be appreciated that it is much easier for a user to access and compress the edges of the release members than it would be for the user to hold each end of the sleeve and compress the sleeve directly.

Further, if one of the release members is held in a fixed position, for example against the body of a patient, it is only necessary for a user to squeeze one of the release members 214, 216 to compress the sleeve 110 and release the line 112.

Figure 3:
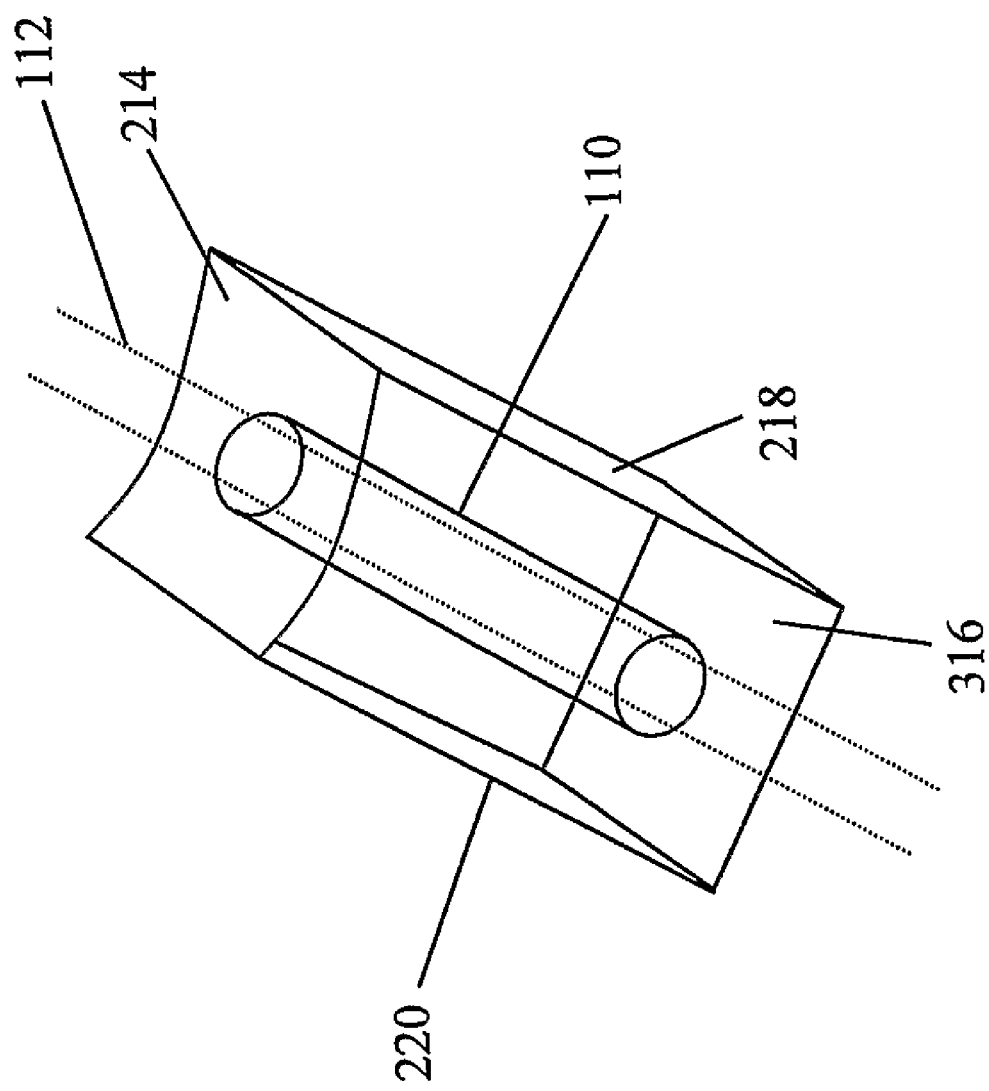
FIG. 3 is a schematic diagram of a line locking device with a release means according to a further embodiment.

A further embodiment is illustrated in FIG. 3 in which one of the release members 316 is provided as a planar surface. In this embodiment, the biasing of the sleeve 110 to a lengthened position is provided by one release member 214, but either member may be compressed and bent inwards to shorten and widen the sleeve 110. The planar release member 316 may be provided with adhesive over its lower surface to secure the locking device, and so the line, to a patient or to equipment.

Figure 4:
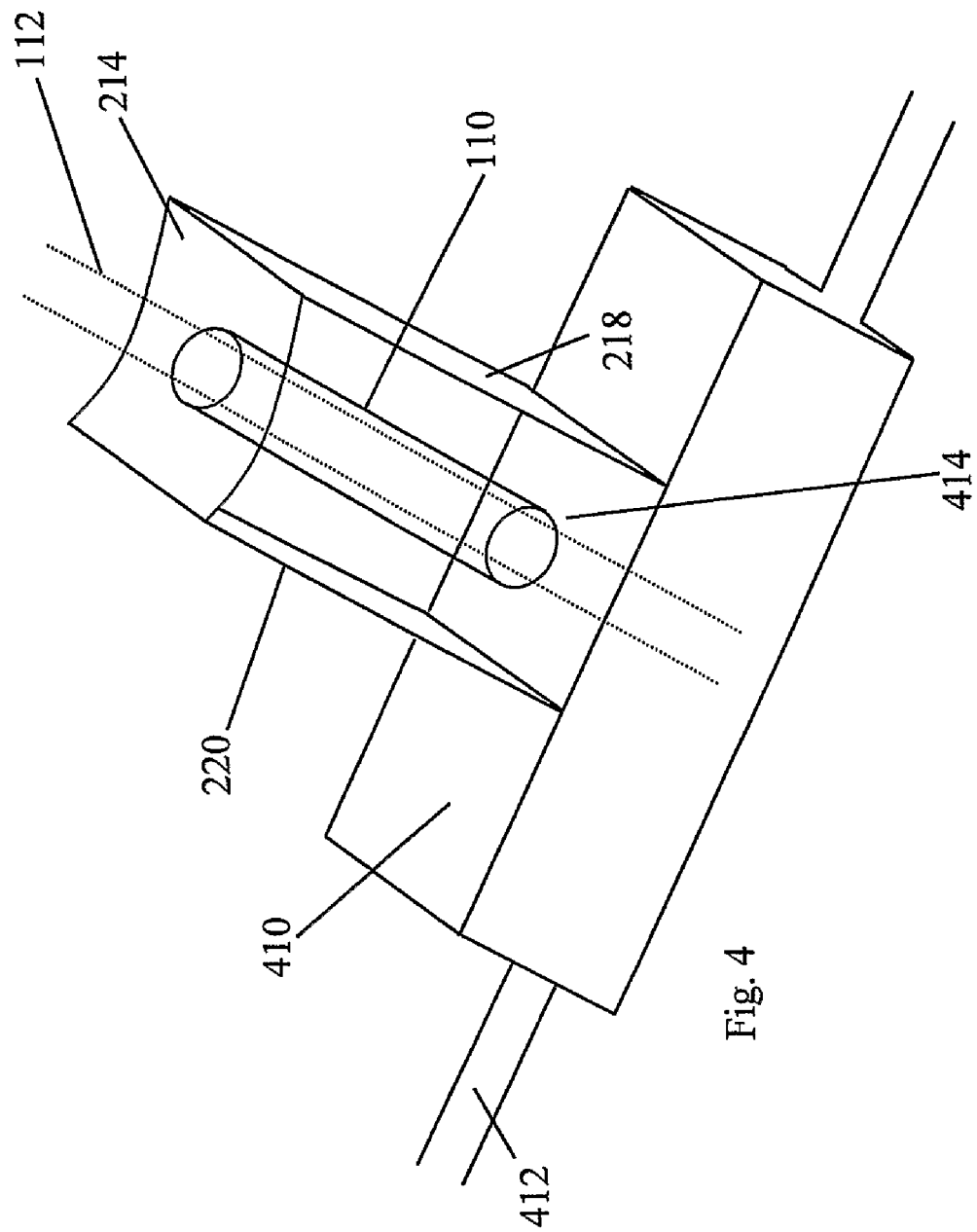
FIG. 4 is a schematic diagram of a line locking device with a release means incorporated into a mouthpiece for a breathing tube according to one embodiment.

FIG. 4 illustrates a further embodiment in which the line locking device is incorporated into a mouthpiece 410 for a breathing tube 112. The end of the sleeve 110 nearest to the patient 414 is held into a fixed position by the mouthpiece 410. The end of the sleeve furthest from the patient is provided with a release member 214, which also biases the sleeve 110 to a lengthened position. The breathing tube 110 may be released to slide within the sleeve 110 by squeezing together the outer edges of the release member 214, longitudinally compressing and widening the sleeve 110. Since only one release member needs to be squeezed to release the line, this operation can be performed single-handedly and in a confined space near to the patient's face.

The line locking device may be releasable from the mouthpiece to enable the ensemble to be applied to and removed from the patient more easily.

Figure 2:
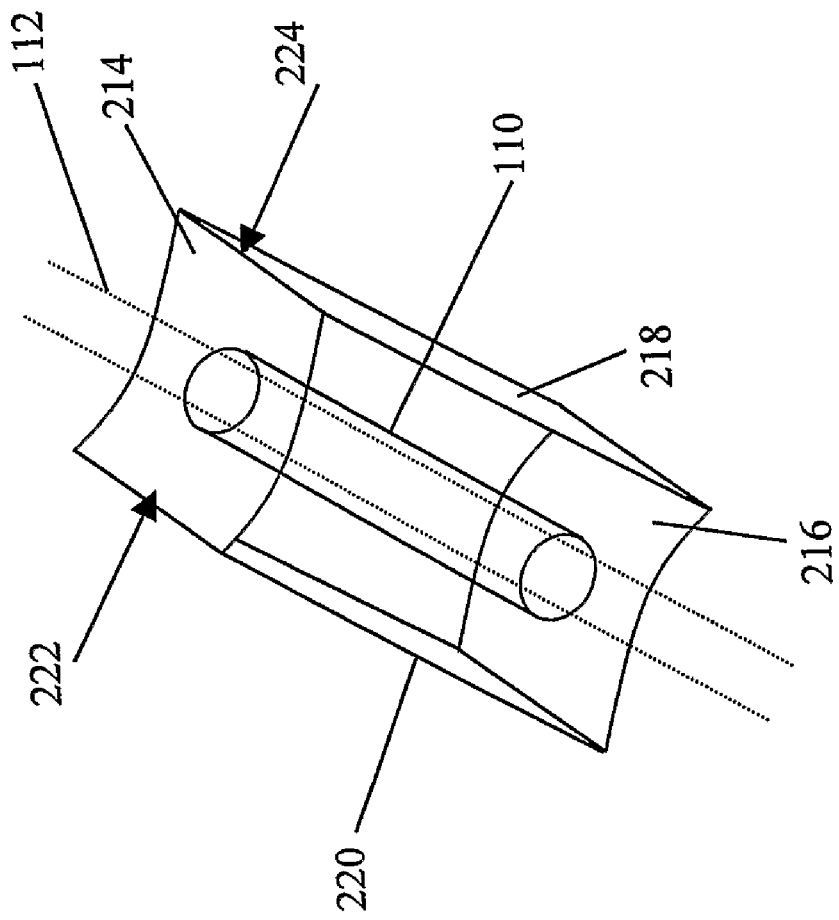
FIG. 2 is a schematic diagram of a line locking device with a release means according to one embodiment.

In further embodiments, the line locking device of FIG. 2 or 3 may be incorporated into other equipment, for example the device may be provided with means to secure the device to a patient's bed or to monitoring equipment.

Figure 15:
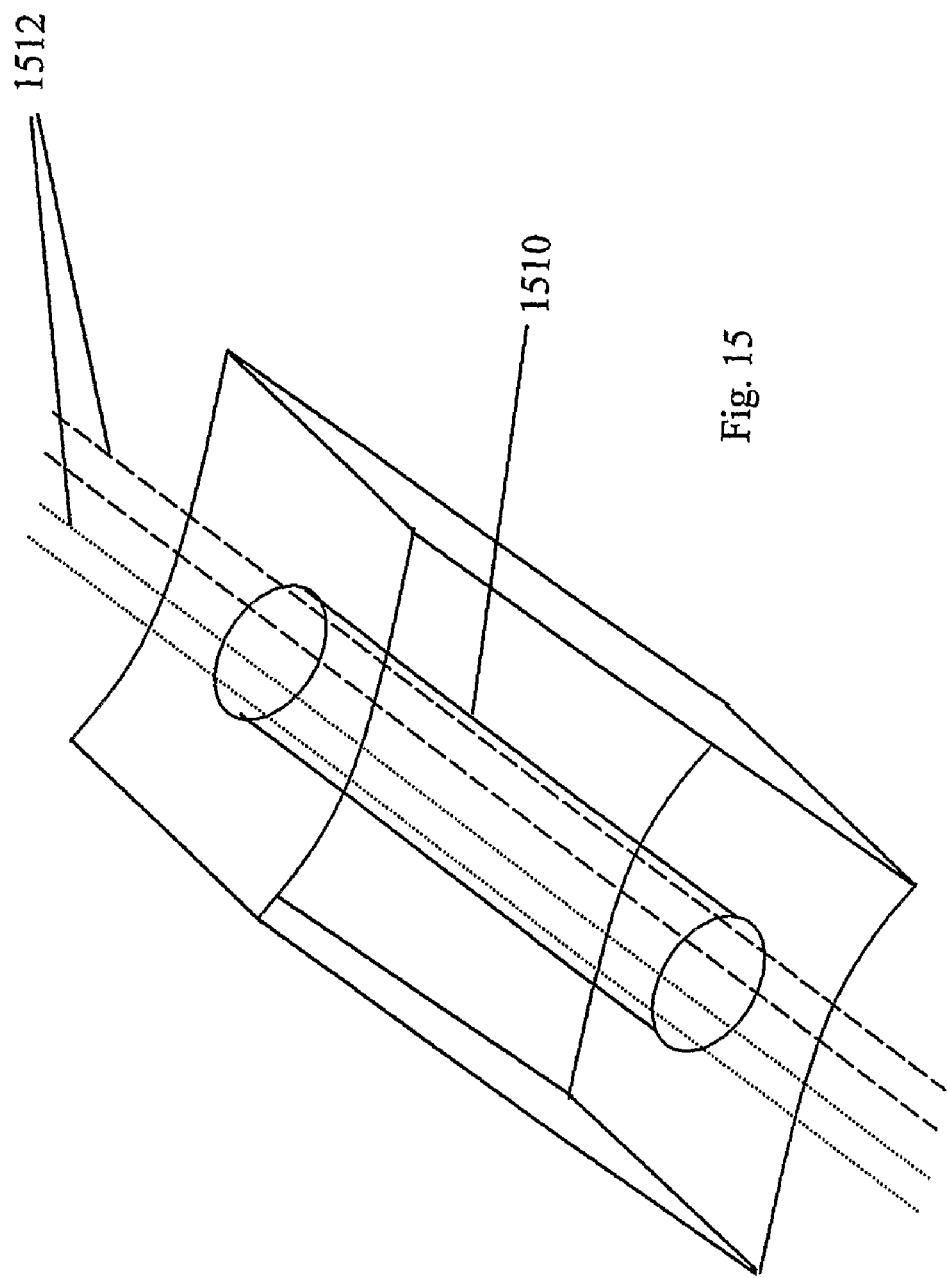
FIG. 15 illustrates a further embodiment of a line locking device.

As illustrated in FIG. 14, a single release means 1410 may be used with a plurality of sleeves 1412 to secure the position of a plurality of lines 1414 relative to a patient. Similarly, as illustrated in FIG. 15, a plurality of lines 1512 may be secured in a single sleeve 1510.

Figure 16:
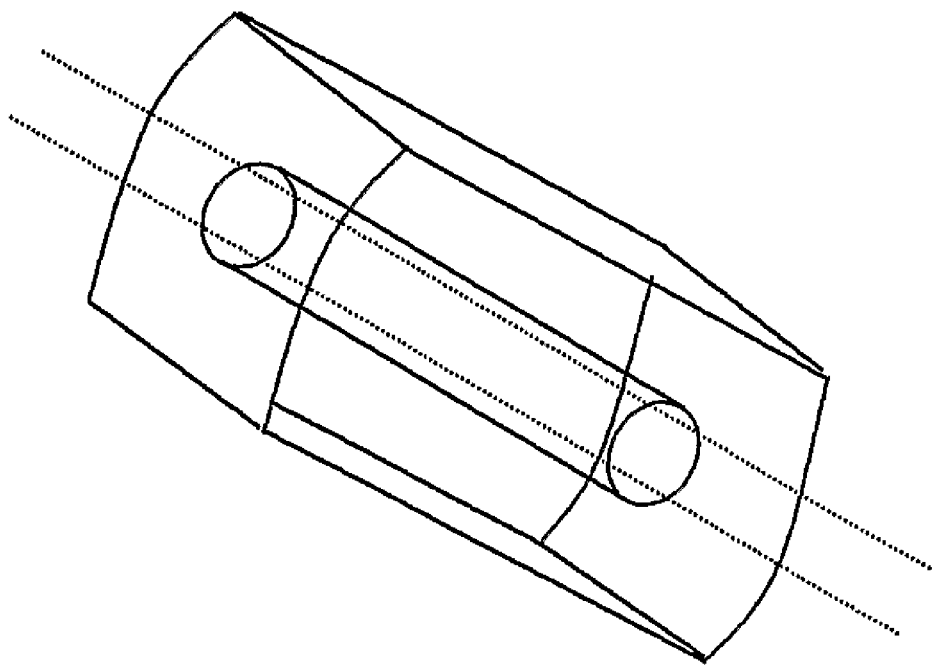
FIG. 16 is a schematic diagram of a further embodiment of a line locking device.

A further embodiment of the line locking device is illustrated in FIG. 16. As illustrated in FIG. 16, one or both of the release means may be biased to a slightly convex position. To release the line, the operator may then have to overcome the convex bias to use the release means to compress the ends of the sleeve together. Hence the sleeve may be secured or locked in an extended position. This may make it more difficult to release the line from the locking device accidentally. A similar result may be achieved by biasing the release means to a planar position.

A further embodiment of the line locking device is illustrated in FIG. 17. In the embodiment of FIG. 17, the release means 1710 are held in a planar configuration, which may provide an initial resistance to movement of the release means. Buttons 1712 are provided on the side support members which connect to rigid arms 1714 arranged between the support members and the sleeve. The rigid arms are in turn connected to flexible rods 1716 or strings held in tension between the release means 1710. Compressing the buttons 1712 on the side support members causes the rigid arms 1714 to move the flexible rods 1716 to a curved position. This draws the centres of the release means 1710 closer together, compressing the sleeve and releasing the line within the sleeve.

In an alternative embodiment, the system described above may be implemented without buttons but with the side support members connected to the rigid arms.

In a further alternative embodiment, the side support members may comprise substantially rigid members hence, any transverse compression or pinching force applied to the side support members will compress the edges of the release members and cause compression of the sleeve. In this way, a larger area may be provided for an operator to compress the sleeve and release the line.

Figure 5:
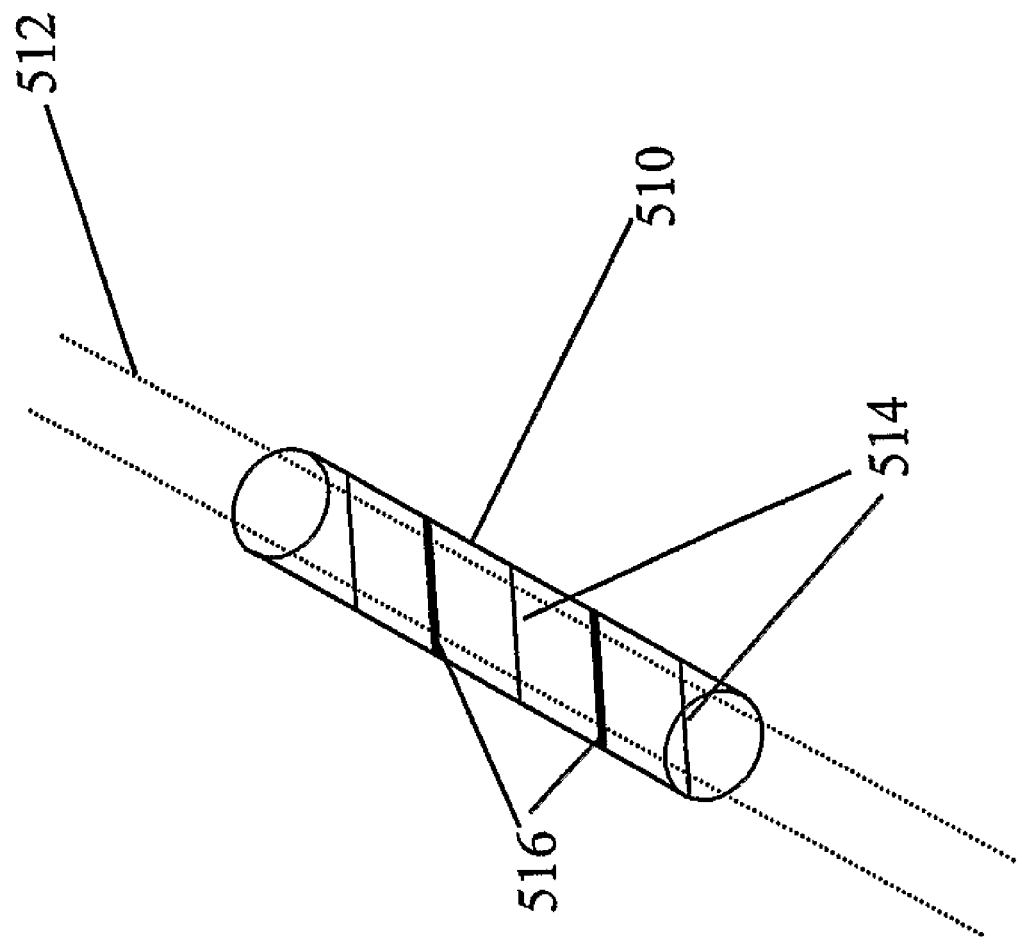
FIG. 5 illustrates a line locking device including a radio opaque marker according to one embodiment.

An embodiment of a line locking device incorporating a marker will now be described with reference to FIG. 5. As described above, the line locking device includes a sleeve 510 into which a line 512, such as a catheter tube, may be inserted. To locate the line locking device, and so the position of the line which passes through it, on an X-ray or other image produced by a remote imaging technique, the line locking device is provided with a marker 514, 516, in this case a radio opaque marker which is reflective to X-rays. In the embodiment illustrated in FIG. 5, the marker comprises two filamentary strands 514, 516 of an X-ray reflective material, or a material covered with an X-ray reflective coating. The strands 514, 516 are woven into the surface of the line locking sleeve 510. In this embodiment, the marker is made more distinctive by providing two strands of different thicknesses woven into sleeve. However, it will be appreciated that any marker configuration may be provided on the line locking device to enable the device to be identified in an image of the patient.

Figure 6:
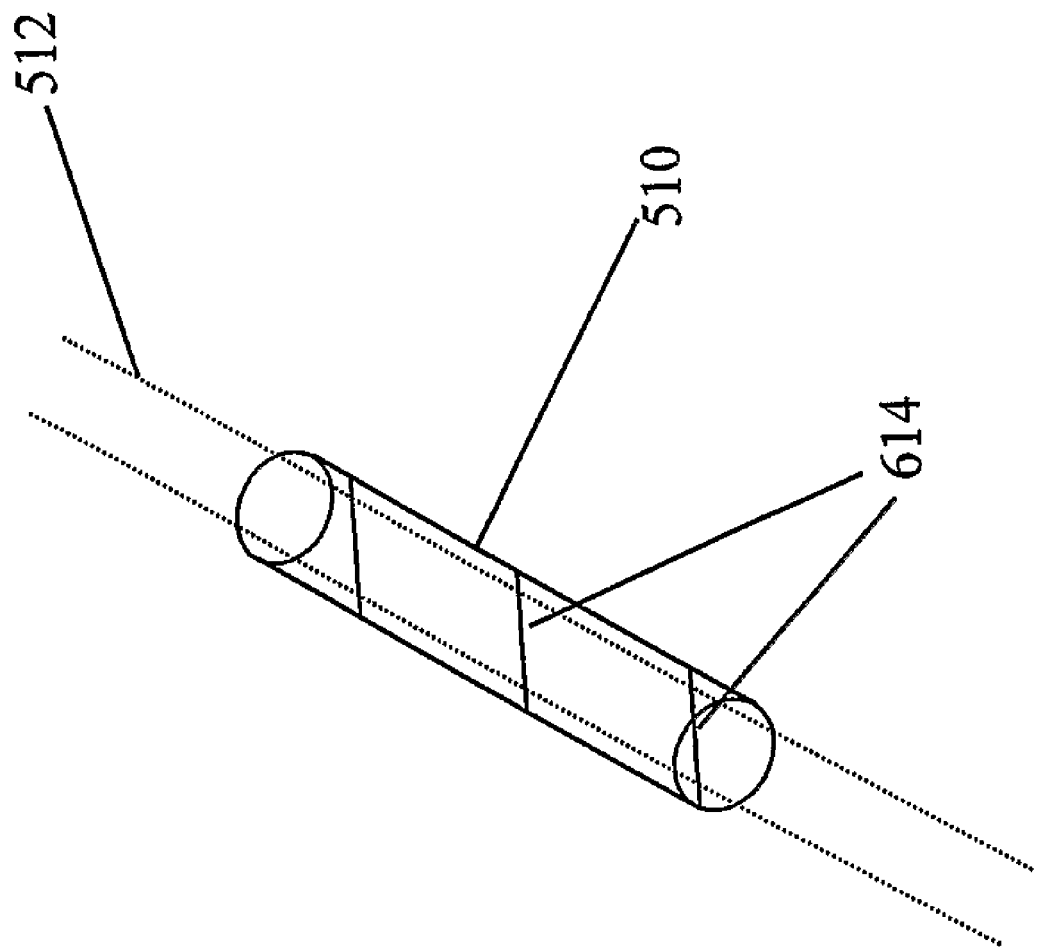
FIG. 6 illustrates a further line locking device including a radio opaque marker according to a further embodiment.

A further embodiment of a line locking device incorporating a marker is illustrated in FIG. 6 in which a single filamentary strand 614 of an X-ray reflective material is woven into the sleeve of the device. The embodiments illustrated in FIGS. 5 and 6 may be used on lines that are located closely together on a patient. Since the markers used on each sleeve are mutually distinct and easily differentiated, the markers would allow the identification of the different lines attached to a patient and their relative locations to be easily identified.

Figure 7:
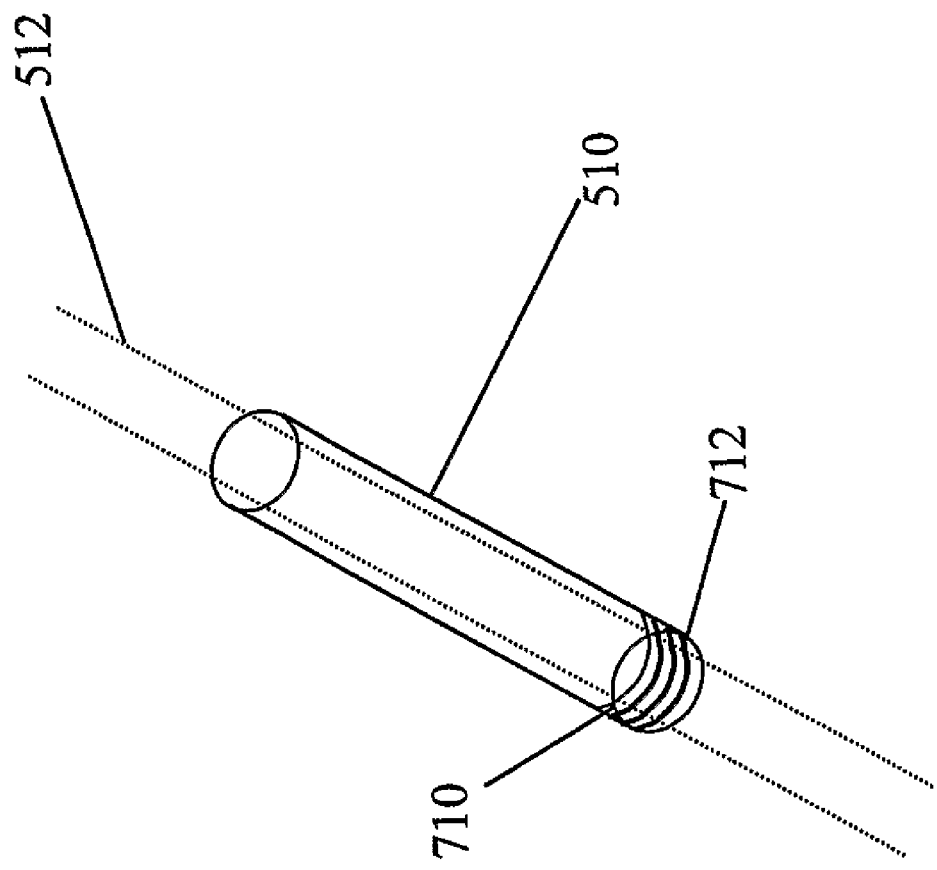
FIG. 7 illustrates a further line locking device including a radio opaque marker according to a further embodiment.

A further embodiment of a line locking device incorporating a marker is illustrated in FIG. 7. In this embodiment, the line locking device is provided with a collar 710 at least one end of the sleeve 510. The collar 710 may provide a rigid surface using which the line locking device may be compressed to cause the sleeve 510 to move over the line 512. In this embodiment, a radio opaque marker, such as an X-ray reflective marker, is provided as lines 712 provided around the collar 710 of the sleeve 510. Hence, it will be appreciated that a marker may be provided on the line locking device in a number of different ways, not limited to the embodiments illustrated herein.

Figure 8:
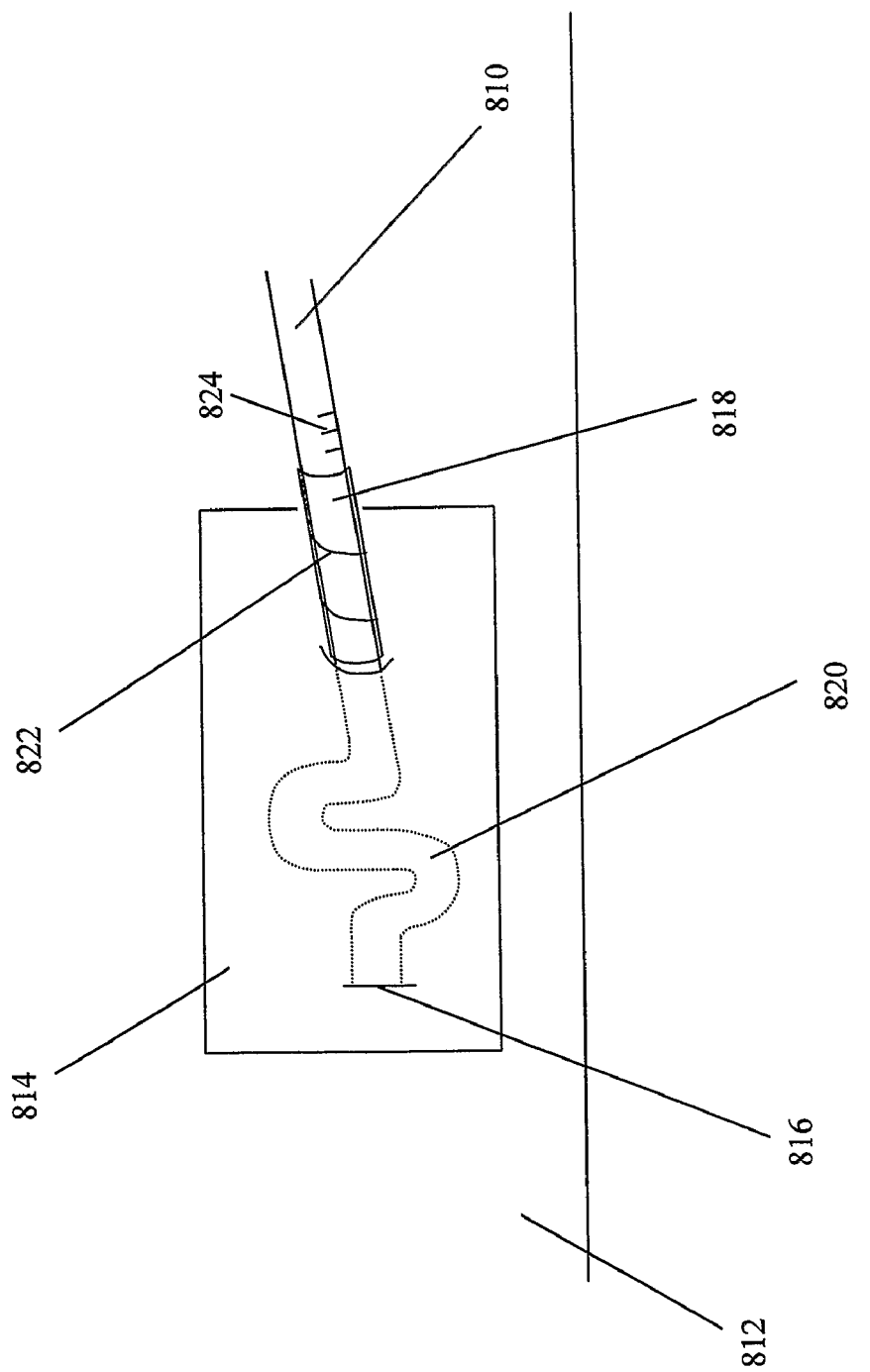
FIG. 8 illustrates a line locking device locking a line into place on a patient according to one embodiment.

One embodiment of a line locking device incorporating a radio opaque marker is illustrated schematically in use in FIG. 8. In the figure, a line 810 is inserted into a patient 812 at an insertion point 816. The insertion point 816 is covered by an opaque dressing 814, so it is not possible to see the section of the line 820 under the dressing 814. When the line 810 is inserted into the patient 812, it may be inserted to a precise depth, which can be determined using gradations 824 provided on the line outside the dressing. An X-ray of this area of the patient's body 812 would show the line 810 and the insertion point of the line 816, but would not show the location of the dressing 814 and hence it would not be possible to determine whether the line 810 was correctly inserted into the patient 812 or whether a portion of the line 820 had become gathered under the dressing 814, beyond the measured gradations 824. However, this problem may be solved by providing a line locking device 818 as illustrated in FIG. 8. The line locking device 818 is provided around the line 810 and locks the line 810 in place relative to the dressing 814, or the patient 812, to which it may be sutured or adhered. The line locking device 818 of FIG. 8 is provided with a marker that is reflective to X-ray radiation in the form of a reflective strand 822 woven into the sleeve of the locking device 818. When an X-ray is now taken of the patient 812, the position of the line locking device 818 will now be easily identifiable using the marker 822, so it will be straightforward to determine the position at which the line 810 enters the dressing 814 relative to the point of entry 816 of the line into the patient 812. Hence any excess section of line 820 under the dressing can be identified and the depth of entry of the line 810 into the patient 812 can be correctly determined, based on the gradations 824, and corrected if necessary.

Figure 9:
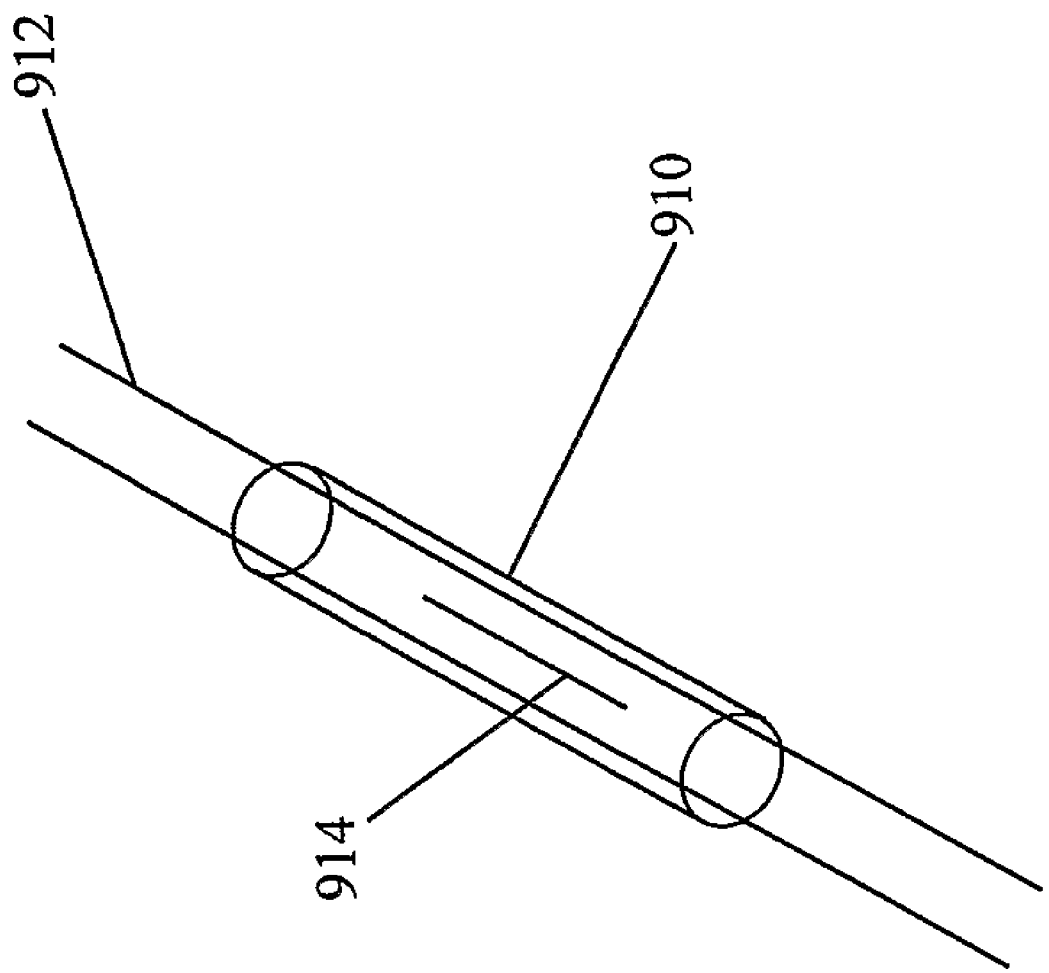
FIG. 9 is a schematic diagram of a line locking device for sealing a split or hole in a line according to one embodiment.

The use of a line locking device as described herein to repair holes or leaks in lines will now be described in more detail with reference to FIG. 9. FIG. 9 illustrates a line for carrying fluids 912, such as a catheter tube or a drip line, having a split 914 along its length. To provide a seal at the location of the split 914, the sleeve 910 of a line locking device is positioned over the split 914 in the line. On release, the sleeve 910 extends longitudinally and contracts radially to grip the line 912 and compress the edges of the split 914 together.

The sleeve 910 may be secured in position by applying adhesive tape (not shown) around the ends of the sleeve 910 and around the line 912. The sleeve may also be provided with a water proof inner layer, or may be manufactured from a water proof material to prevent leakage of the fluids from the line 912.

The selection of the stiffness of the sleeve will now be discussed in more detail with reference to FIGS. 10a and 10b. FIG. 10a illustrates a line locking device 1010 in place around a line 1012 attached to a patient 1018. Pressure 1014 is applied to the line 1012 in a direction towards the line locking device 1012 and towards the patient 1018. The applied pressure 1014 may be applied purposefully or may be due to, for example, normal movement of the patient 1018.

Figure 10B:
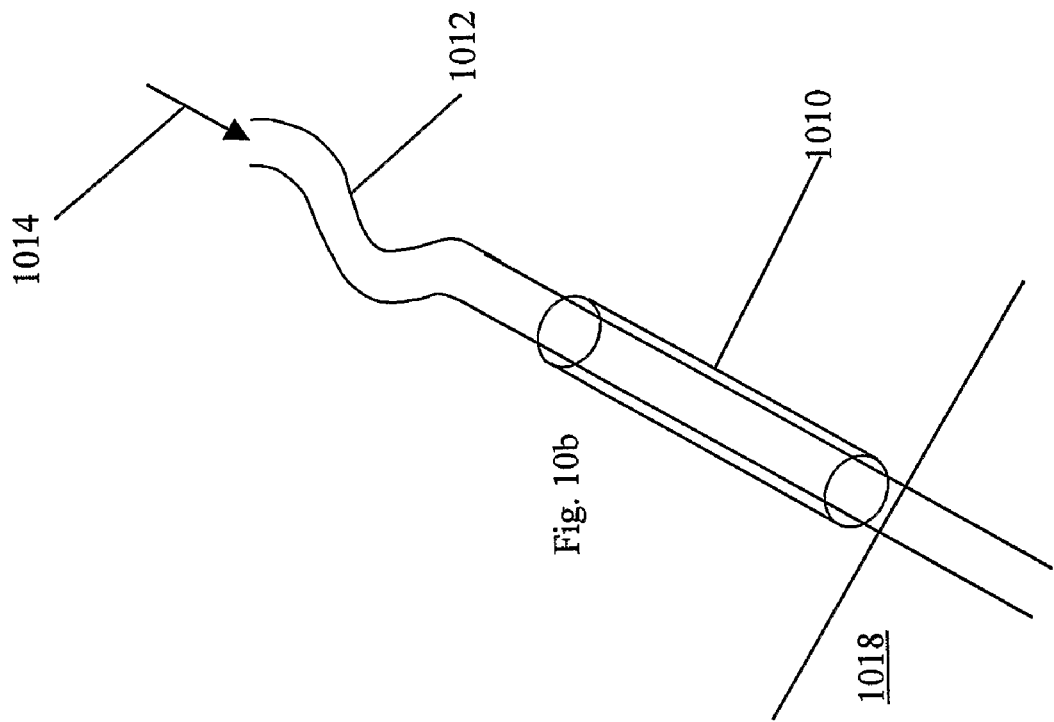
FIGS. 10a and 10b illustrate schematically the process of pushing a line towards a line locking device.
Figure 10A:
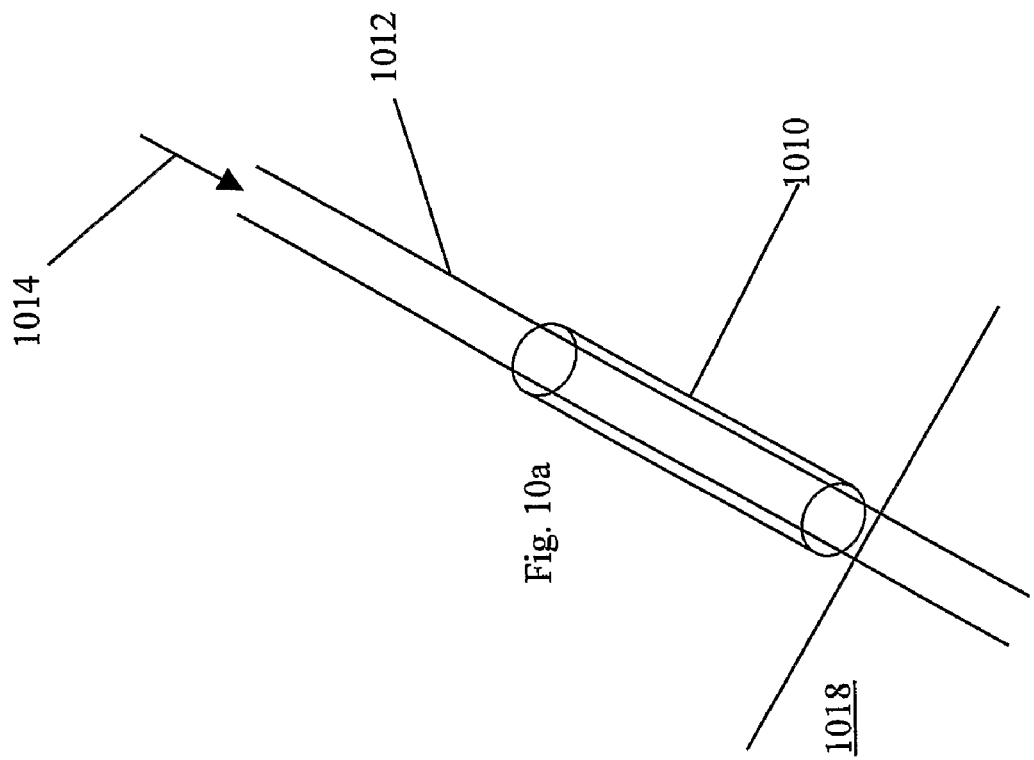

FIG. 10b illustrates the result of applying pressure to the line. Since the stiffness of the sleeve of the line locking device 1010 is selected to be greater than the stiffness of the line 1012, the line bends before there is any bending or compression of the line locking device 1010. Hence any 'creep' of the line 1012 through the line locking device 1010 is reduced.

In particular, the stiffness of the braid or weave of the sleeve of the line locking device 1010 may be selected to be greater than the stiffness of the line 1012

In this way, movement of the line 1012 through the line locking device 1010 may be achieved only by deliberate compression of the line locking device 1010 to shorten and widen the sleeve and allow the line 1012 to move freely through the sleeve.

The force required to cause a tubular line to buckle can be calculated based on the Area Moment of Inertia of the tubing, the Youngs Modulus of the material of the tube and the length of the tube.

The Area Moment of Inertia, I, of a tube can be calculated based on the internal diameter, $D_0$, and the external diameter, $D_1$, of the tube using the formula:

$$I=\pi/64*(D_0^4-D_1^4)$$

The buckling load, T, can then be calculated based on the Area Moment of Inertia, I, the Youngs Modulus of the material from which the tube is made, E, and the distance along the tube at which the force is applied, L. Then, $$T=-\pi^2*(EI/L^2)$$

For a plastic tube, having an internal diameter of 4 mm, an external diameter of 5 mm, a Youngs Modulus of around $2.5*10^9$ Nm$^{-2}$ and a length of 10 cm, the buckling force T is around 45N.

Hence, for a line having the parameters set out above, the force required to compress the line locking device and so to expand the sleeve radially and allow the line to slide through the sleeve must be greater than 45N. In practice, in many embodiments, the force required to compress the sleeve is likely to be significantly greater than this.

For a force applied at 15 cm from the line locking device, the buckling force falls to around 20N and for a force applied at 30 cm, the buckling force falls further to around 5N. For a force applied at only 8 cm from the line locking device, however, the buckling force required to cause the line to buckle is around 70N.

It will be appreciated that both the force required to compress the device and the maximum tension that the locking device can support without slipping along the line may be varied depending on the intended use for the locking device. For example, the gripping force required to be exerted by a line locking device for use with equipment attached to a neonatal baby is likely to be much less than the required gripping force for equipment attached to an adult patient. Hence the line locking device for an adult patient may be designed to require a greater force to compress the sleeve and release the line than a line locking device for use with a baby.

It will be clear to one skilled in the art that elements of the embodiments described above may be provided independently or in combination and variations of the embodiment described may be provided.

The invention claimed is:

1. Apparatus for securing a line, comprising at least one sleeve of variable length capable when lengthened of gripping the line and when shortened of sliding along the line, the device further comprising release means arranged to shorten the sleeve on application of a compressive force to the release means in a direction substantially transverse to the longitudinal direction of the sleeve, the release means including biasing means configured to bias the sleeve toward a lengthened position.

2. Apparatus according to claim 1 further comprising means to secure the apparatus directly to a patient.

3. Apparatus according to claim 1 further comprising means to secure the apparatus to furniture or equipment associated with a patient.

4. Apparatus according to claim 1 wherein the release means is operable from one end of the sleeve.

5. Apparatus according to claim 1 wherein the release means is operable from either end of the sleeve.

6. Apparatus according to claim 1 wherein the release means is attached to attachment points at the ends of the sleeve and wherein the application of a compressive force to the release means brings the attachment points closer together.

7. Apparatus according to claim 1 wherein the compressive force applied to the release means to shorten the sleeve is less than the longitudinal force required to shorten the sleeve.

8. Apparatus according to claim 1 wherein the compressive force is applied to the release means by manually pinching a portion of the release means.

9. Apparatus according to claim 1 wherein the release means comprises a flexible member attached to the sleeve.

10. Apparatus according to claim 9 wherein the member is arranged so that a compressive force applied to the member in a direction substantially transverse to the longitudinal direction of the sleeve bends the member and shortens the sleeve.

11. Apparatus according to claim 10 wherein the compressive force is applied along the outer edges of the member by pinching the outer edges of the member together.

12. Apparatus according to claim 9 wherein the member is held in a concave position when the sleeve is at its maximum length to bias the sleeve to a lengthened position.

13. Apparatus according to claim 1 wherein one end of the sleeve is coupled to a mouthpiece for breathing apparatus.

14. Apparatus according to claim 1 wherein the release means is arranged to provide an initial resistance to movement on application of the compressive force.

15. Apparatus according to claim 1 wherein the apparatus comprises a plurality of sleeves for securing a plurality of lines.

16. Apparatus according to claim 1 wherein the sleeve comprises a braided tubular sleeve.

17. Apparatus according to claim 1 further comprising a marker opaque to radiation.

18. Apparatus for securing the position of a flexible line with respect to a patient, the apparatus comprising a flexible line and a sleeve of variable length capable when lengthened of gripping the line and when shortened of sliding along the line, wherein the force required to shorten the sleeve is greater than the force required to cause the flexible line to buckle.

* * * * *